United States Patent [19]
Yanof et al.

[11] Patent Number: 6,064,904
[45] Date of Patent: May 16, 2000

[54] FRAMELESS STEREOTACTIC CT SCANNER WITH VIRTUAL NEEDLE DISPLAY FOR PLANNING IMAGE GUIDED INTERVENTIONAL PROCEDURES

[75] Inventors: Jeffrey H. Yanof, Solon; Paul H. Klahr, Beachwood, both of Ohio; Lauren O'Donnell, Estero, Fla.

[73] Assignee: Picker International, Inc., Highland Heights, Ohio

[21] Appl. No.: 08/980,337

[22] Filed: Nov. 28, 1997

[51] Int. Cl.[7] .................................................. A61B 5/00
[52] U.S. Cl. ........................ 600/414; 600/429; 606/130
[58] Field of Search .................................. 600/427, 429, 600/426, 411, 414, 417; 606/130

[56] References Cited

U.S. PATENT DOCUMENTS

| | | | |
|---|---|---|---|
| 4,583,538 | 4/1986 | Onik et al. | 600/429 |
| 4,791,934 | 12/1988 | Brunnett | 128/653 |
| 5,078,140 | 1/1992 | Kwoh | 128/653.1 |
| 5,099,846 | 3/1992 | Hardy | 128/653.1 |
| 5,142,930 | 9/1992 | Allen et al. | 74/469 |
| 5,155,435 | 10/1992 | Kaufman et al. . | |
| 5,230,338 | 7/1993 | Allen et al. | 128/653 |
| 5,309,913 | 5/1994 | Kormos et al. | 128/653.1 |
| 5,398,684 | 3/1995 | Hardy | 128/653.1 |
| 5,524,180 | 6/1996 | Wang et al. | 600/118 |
| 5,533,082 | 7/1996 | Groönemeyer et al. | 378/20 |
| 5,590,655 | 1/1997 | Hussman | 128/653.1 |
| 5,598,269 | 1/1997 | Kitaevich et al. | 356/399 |
| 5,622,170 | 4/1997 | Schulz | 128/653.1 |
| 5,628,327 | 5/1997 | Unger et al. | 128/749 |
| 5,647,373 | 7/1997 | Paltieli | 128/749 |
| 5,657,429 | 8/1997 | Wang et al. | 395/86 |
| 5,868,675 | 2/1999 | Henrion et al. . | |

FOREIGN PATENT DOCUMENTS

| | | |
|---|---|---|
| 0 676 178 | 10/1995 | European Pat. Off. . |
| 0 728 446 | 8/1996 | European Pat. Off. . |
| 2 660 185 | 10/1991 | France . |
| 2 692 466 | 12/1993 | France . |
| WO 9104711 | 4/1991 | WIPO . |
| WO 97/42898 | 11/1997 | WIPO . |

*Primary Examiner*—Ruth S. Smith
*Attorney, Agent, or Firm*—Fay, Sharpe, Fagan, Minnich & McKee, LLP

[57] ABSTRACT

A frameless stereotactic CT scanner includes a virtual needle display for planning image-guided interventional procedures. The virtual needle is useful for planning the introduction of an object such as a biopsy probe into a patient at an entry point along a trajectory to a target point within the patient. Using an imaging device, the patient is scanned to generate an image volume data set of an area of the patient. Using a stereotactic mechanical arm assembly mounted on one end to the imaging device, a surgical planning device is positioned adjacent the patient on the imaging device. A display includes a first transverse axial view of the patient taking through an image slice corresponding to the virtual needle entry point on the patient and, a second transverse axial view of the patient taken on an image slice of the image volume data set corresponding to a target point within the patient. A first oblique axial/coronal view is also displayed together with the first and second transverse axial views, the oblique coronal view being co-planar with the virtual needle trajectory and closest to the coronal axis. An oblique sagittal view is displayed together with the above images, the oblique sagittal view being co-planar with the virtual needle. A manually adjustable virtual needle depth control member is used to adjust the "length" of a virtual needle displayed within the image volume data set. Each of the views displayed are simultaneously updated to reflect the then current position and orientation of a surgical planning device on a stereotactic mechanical arm assembly.

36 Claims, 7 Drawing Sheets

FRAMELESS STEREOTACTIC CT SCANNER WITH VIRTUAL NEEDLE DISPLAY FOR PLANNING IMAGE GUIDED INTERVENTIONAL PROCEDURES

BACKGROUND OF THE INVENTION

The present invention relates to the art of interactive image-guided surgery. It finds particular application in conjunction with the planning stage of minimally invasive stereotactic surgery performed in CT imaging systems using guide devices to orient surgical tools such as biopsy probes or the like and will be described with particular reference thereto. It is to be appreciated, however, that the invention is also applicable to a wide range of imaging equipment and minimally invasive stereotactic surgical procedures including, for example, ultrasonic and magnetic resonance imaging devices and surgery performed using those devices.

Heretofore, several systems have been proposed combining mechanical arm type mechanisms together with human anatomy imaging devices for performing certain interventional surgical procedures such as, for example, the placement of catheters, drainage tubes, biopsy probes, or the like, within a patient's body. U.S. Pat. No. 5,142,930 teaches a mechanical arm device associated with an imaging system generating one or more images of a patient's anatomy and displaying those images on a screen. A computer is used to track the location of a surgical tool connected to the mechanical arm as the arm is moved through physical space. The computer performs a transforming rotation of the physical space to the image space in order to cause the display device to show the location of the surgical tool within the patient's image space. Position feedback devices are arranged on the mechanical arm for tracking the end tip of a tool on the arm relative to the position of fiducial implants disposed on or in the patient's body.

One disadvantage of the above system, however, is that the interventionist is not provided with a plurality of alternative views of the target within the patient. It would be desirable to simultaneously display views of the target within the patient, the entry point of a real or "virtual" needle on the patient's skin, and the trajectory of the virtual or biopsy needle therebetween. A frameless stereotactic CT scanner with a virtual needle co-axial with a surgical planning instrument and displayed on a monitor in the scanner room would greatly improve the planning stages of image-guided interventional procedures. A virtual needle that is displayed through multiple planes extending through a patient's image data volume set would provide an interventionist with an enhanced understanding of the path between the entry point and the target for the avoidance of damage to arteries or the like and obstructions such as bone.

U.S. Pat. No. 5,622,170 teaches a surgical apparatus for determining the position and orientation of an invasive portion of a surgical probe within a patient's body. A computer associated with that system determines the position and orientation of the invasive portion of the surgical tool by correlating the position of the tool relative to a predetermined coordinate system with a position of a model of the patient's body defined in relation to the predetermined coordinate system. During use of the above device, however, the interventionist is presented with only a single slice view of the position of the tool tip within a patient's body image.

It would be desirable to perform image-guided minimally invasive stereotactic surgical planning procedures with the advantage of multiple views of the path of a virtual needle defining a trajectory from an entry point on a patient's skin to a target image within the patient's body. In addition, it would be desirable to provide an automatic transformation between a surgical planning device in a localizer space and a patient image data set in image space so that the position of the surgical planning device is displayed as a virtual needle within the image of the patient. To best assist interventionists in positioning surgical instrument guide devices, the virtual needle is displayed on multiple screen portions of a display monitor or the like located in the scan room. It would also be desirable to provide a knob or other mechanism such as a manual slider for use by an interventionist to "extend" and "retract" the virtual needle in the multiple displays to quickly and easily chart various approach angles and orientations for planning interventional procedures.

An apparatus capable of determining desired coordinates in an image for use in either functional stereotactic or morphological procedures is taught in U.S. Pat. Nos. 5,398,684 and 5,099,846. The desired coordinates may include, for example, an entry point, a target or placement point, and a trajectory of a probe or the like. According to those patents, a surgeon can determine an optimum probe implantation trajectory using either one of a pair of equivalent methods. In the first method, the entry point of the probe is designated by "tacking" it on the image. A target point on another scanner image slice is selected and the coordinates of the two points are then used to determine a probe's spatial trajectory. In the second method, the trajectory of the probe is defined by entering the probe's angles according to the design of a stereotactic frame. A target point on one image slice is chosen. Next, the angles of the probes spatial interception with that point are entered into a computer. This defines the probe's spatial trajectory.

FIGS. 4, 6, and 8 illustrate sagittal and transverse axial views of a simulated probe trajectory and positioning regarding a tumor in a patient's brain. The views have limited utility because they are not updated simultaneously with movement of a surgical planning device over a patient's body such as by an interventionist using the planning device to manually search for an optimum needle insertion path.

It would be desirable to provide an imaging device with a set of virtual needle displays for planning image-guided interventional procedures. Preferably, the "length" of the virtual needle is manually adjustable by the interventionist using a knob or slide mechanism within reach of a surgical planning device on the end of a stereotactic mechanical arm.

The present invention provides new and improved methods and apparatus for planning image-guided interventional procedures which overcome the above-referenced problems and others.

SUMMARY OF THE INVENTION

In accordance with the present invention, a method of planning a minimally invasive surgical procedure is provided. Using an imaging device, a patient is scanned to generate an image volume data set of an area of the patient. The image volume data set is formed of a plurality of two-dimensional image slices of the patient spaced apart along an axial axis aligned substantially with the toe-to-head axis of the patient. A surgical planning device attached to a stereotactic mechanical arm assembly is positioned adjacent the patient disposed on the imaging device. A first transverse axial view of the patient is displayed together with a second transverse axial view on a display monitor. The first transverse axial view is a display of a first two-dimensional image slice from the plurality of two-dimensional image slices of the patient where the linear trajectory of a virtual needle intersects the patient's body defining a patient virtual entry point. The second transverse axial view is an image slice from the plurality of two-dimensional image slices of the patient where the virtual needle linear trajectory intersects the patient's body at a first virtual target point within the patient.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof, and wherein.

DETAILED DESCRIPTION OF THE PREFERRED EMBODIMENT

Figure 1:
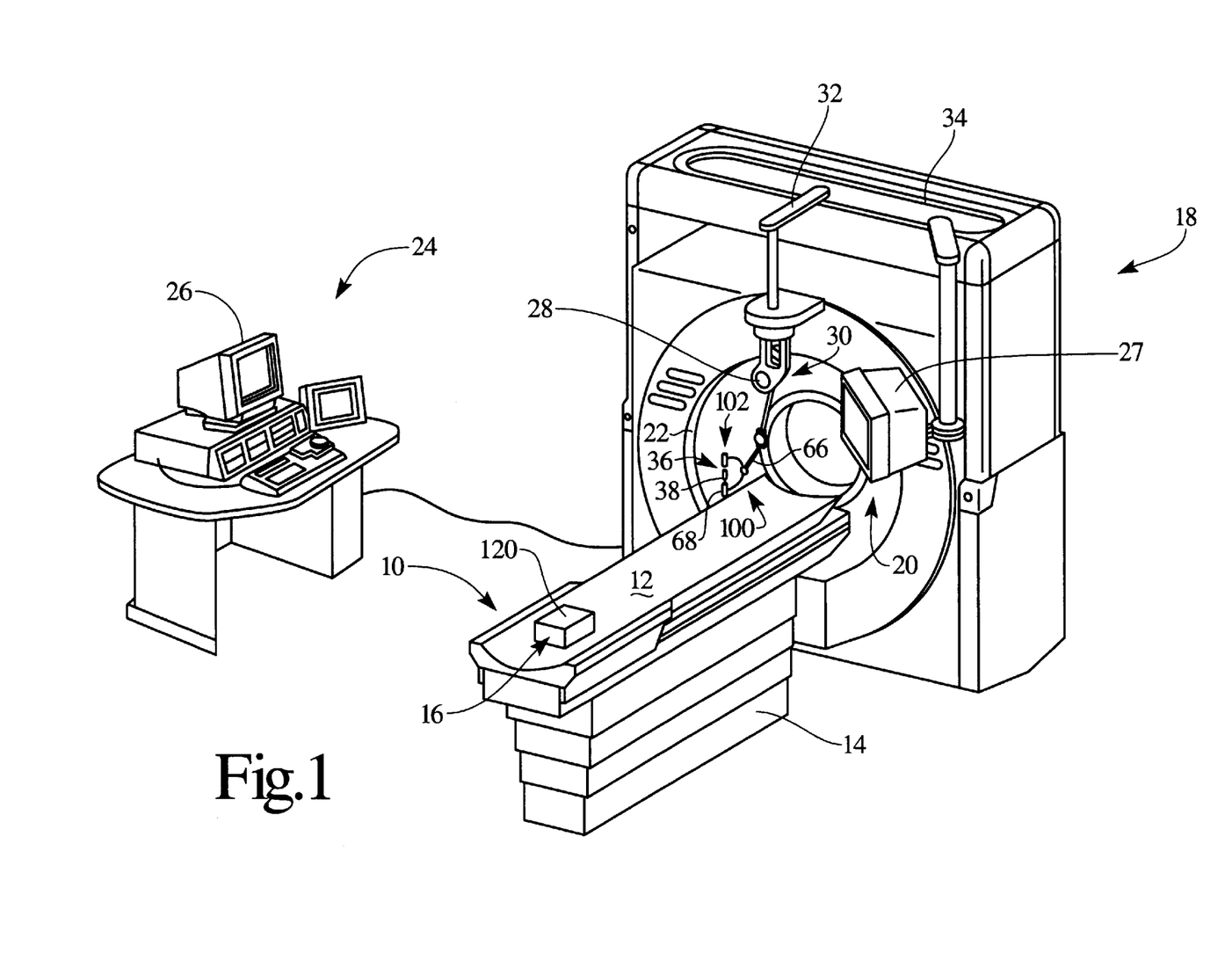
FIG. 1 is a diagrammatic illustration of a frameless stereotactic scanner system including an arm apparatus for image guiding surgical instruments in accordance with the present invention.

Referring now to the drawings wherein the showings are for the purposes of illustrating the preferred embodiments of the invention only and not for purposes of limiting same, with reference first to FIG. 1, a patient table or support 10 includes a patient supporting surface 12 that is mounted for longitudinal movement relative to a base portion 14. The base portion 14 includes a motor for raising and lowering the patient support surface 12 and for moving the patient support surface longitudinally. Position encoders are also provided for generating electrical signals indicative of the height and longitudinal position of the patient support. The patient support includes a calibration and verification area 16 disposed at a known, fixed location. The calibration and verification area is adapted to receive a calibration phantom for calibrating the system in accordance with the present invention and in a manner subsequently described.

A planning, preferably a volumetric diagnostic imaging apparatus 18 is disposed in axial alignment with the patient table such that a patient or subject on the patient support surface 12 can be moved into and through a bore 20 of the volumetric imager. In the illustrated embodiment, the volumetric imager is a CT scanner which includes an X-ray tube mounted for repeated circular travel within a preselected plane. The X-ray tube projects a fan-shaped beam of radiation through a ring 22 of radiation translucent material, through the patient support 12, through a region of interest of the subject, and to a ring or arc of radiation detectors positioned opposite the X-ray tube. As the X-ray tube rotates within the plane, a series of data lines are generated, which data lines are reconstructed into at least a slice image by a reconstruction processor included in a control console 24. The control console is typically remotely located in a shielded room adjacent the scan room. More specifically to the preferred embodiment, the patient support 12 moves longitudinally as the X-ray tube is rotating around the subject such that a selected volume of the patient is scanned along a spiral path or a series of slices. The position of the X-ray tube is monitored by a rotational position encoder, and the longitudinal position of the patient support is monitored by a longitudinal position encoder within the table 10. The reconstruction processor reconstructs a volumetric image representation from the generated data lines. The control console 24 typically includes one or more monitors 26 and various standard operator input devices such as a keyboard, trackball, mouse, or the like. An interventionist control and display console 27 is supported from overhead on a track atop the CT scanner.

A mechanical frameless stereotactic arm assembly is supported from overhead by a carriage 32 movable on an oval track system 34 affixed to the top of the volumetric diagnostic imaging apparatus 18 as generally shown. The carriage is preferably lockable in one or more predetermined fixed locations on the oval track so that a minimally invasive surgical instrument 36 carried on an interchangeable surgical instrument guidance device 100 formed in accordance with the present invention can be positioned in monitored positions and orientations by an interventionist in preparation for and in carrying out a surgical procedure. The surgical instrument illustrated in the FIGURE includes a manual surgical planning device 102 (FIG. 2) constructed with a "V" groove 104 defining a guide path along a linear trajectory 106. Overall, however, the position and orientation of the surgical planning device with respect to a patient on the table are determined by the position of the mechanical arm assembly 30 and the location of the carriage 32 on the oval track system 34.

Figure 2:
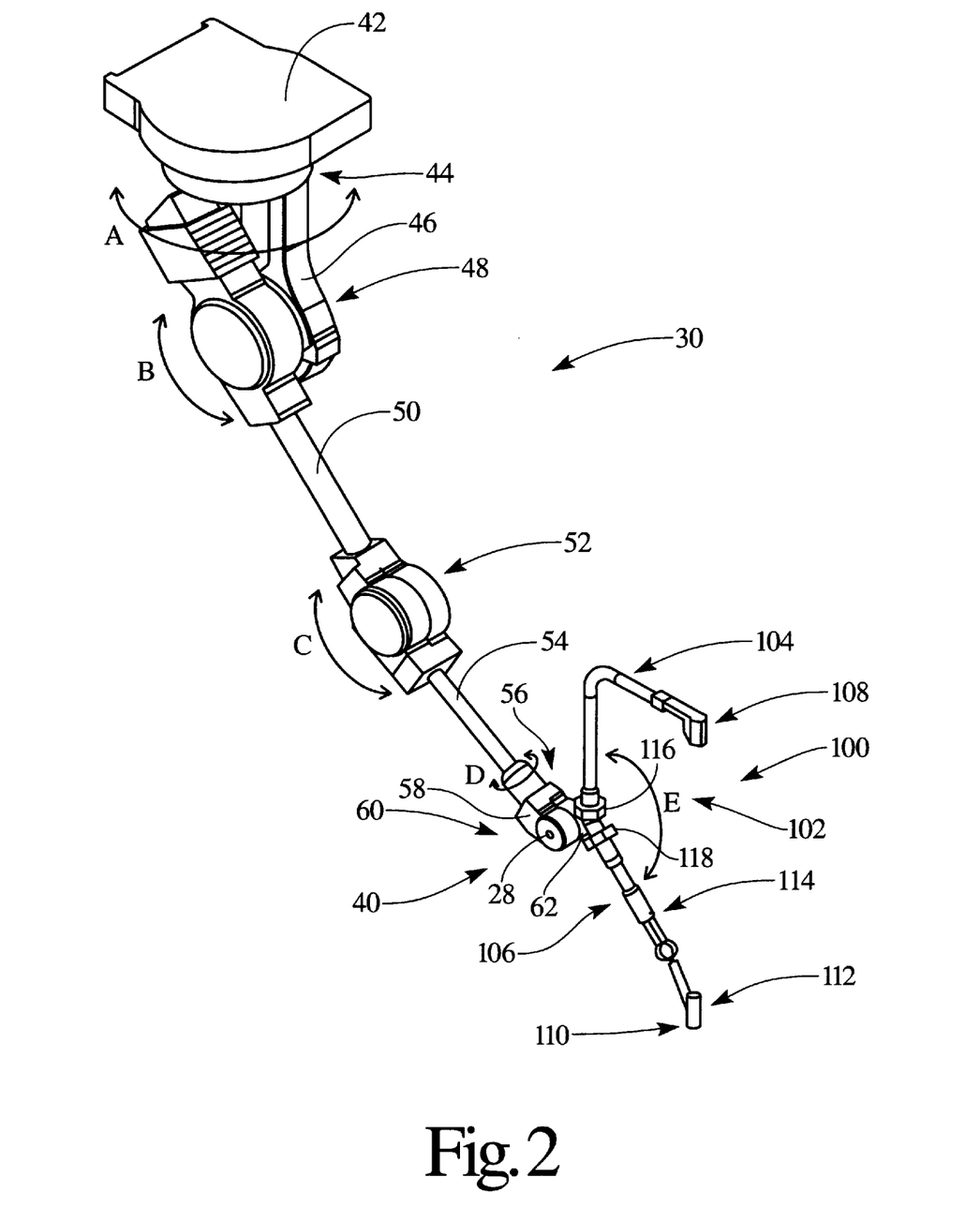
FIG. 2 is a perspective view of the frameless mechanical arm assembly carrying a guidance device formed in accordance with the present invention.

The frameless stereotactic arm assembly 30 is shown generally in FIG. 2 and includes a plurality of arm segments which are interconnected by pivot members forming joints between the arm segments. In that way, a free end 40 of the arm is selectively movable in multiple orientations as necessary to position the surgical instrument 36 (FIG. 1) into various desired positions over the patient support 12. A base member 42 is rigidly connected to the carriage 32 using suitable fasteners, epoxies, or the like. A base joint 44 permits rotation of a primary support member 46 in a direction marked A. Similarly, from the immovable base end of the arm, a shoulder joint 48 permits rotation of an upper arm member 50 in a direction marked B, an elbow joint 52 permits rotation of a lower arm member 54 in a direction marked C, a forearm joint 56 permits rotation of a knuckle member 58 in a direction marked D, and, lastly, a wrist joint 60 permits rotation of a wrist member 62 in a direction marked E.

In accordance with the present invention, at least one position resolver, preferably an optical incremental encoder, is provided at each joint of the mechanical arm assembly 30 to monitor increment articulation and rotation of the arms relative to each other for reasons that will subsequently become apparent. The optical incremental encoders generate feedback pulses indicative of the relative angular and rotational position of the various arm members with respect to each other in a well known manner. The feedback pulses are carried back to an imaging apparatus control circuit using suitable wires or flexible shielded cables extending through the multiple members of the arm assembly. In that way, the position and orientation of the wrist member 62 with respect to the imaging apparatus reference frame and the volumetric image representation obtained by the imaging apparatus.

The position and orientation of surgical instruments carried by the arm assembly relative to the imaging apparatus reference frame and the volumetric image representation obtained by the imaging apparatus are resolved by providing interchangeable surgical instrument guidance devices 100 having a unique identification signal. The identification signal is used by the imaging apparatus control circuit to index a look up table for retrieving various physical dimensional and other functional parameters corresponding to the one or more guidance devices connected to the wrist member 62. In this manner, the physical dimension and other functional parameters, together with the mechanical interconnection which is measured by the resolvers and encoders, provides an accurate indication of the position and orientation of the guidance device 100 relative to the CT scanner and, hence, relative to the image acquired by the CT scanner.

Figure 3:
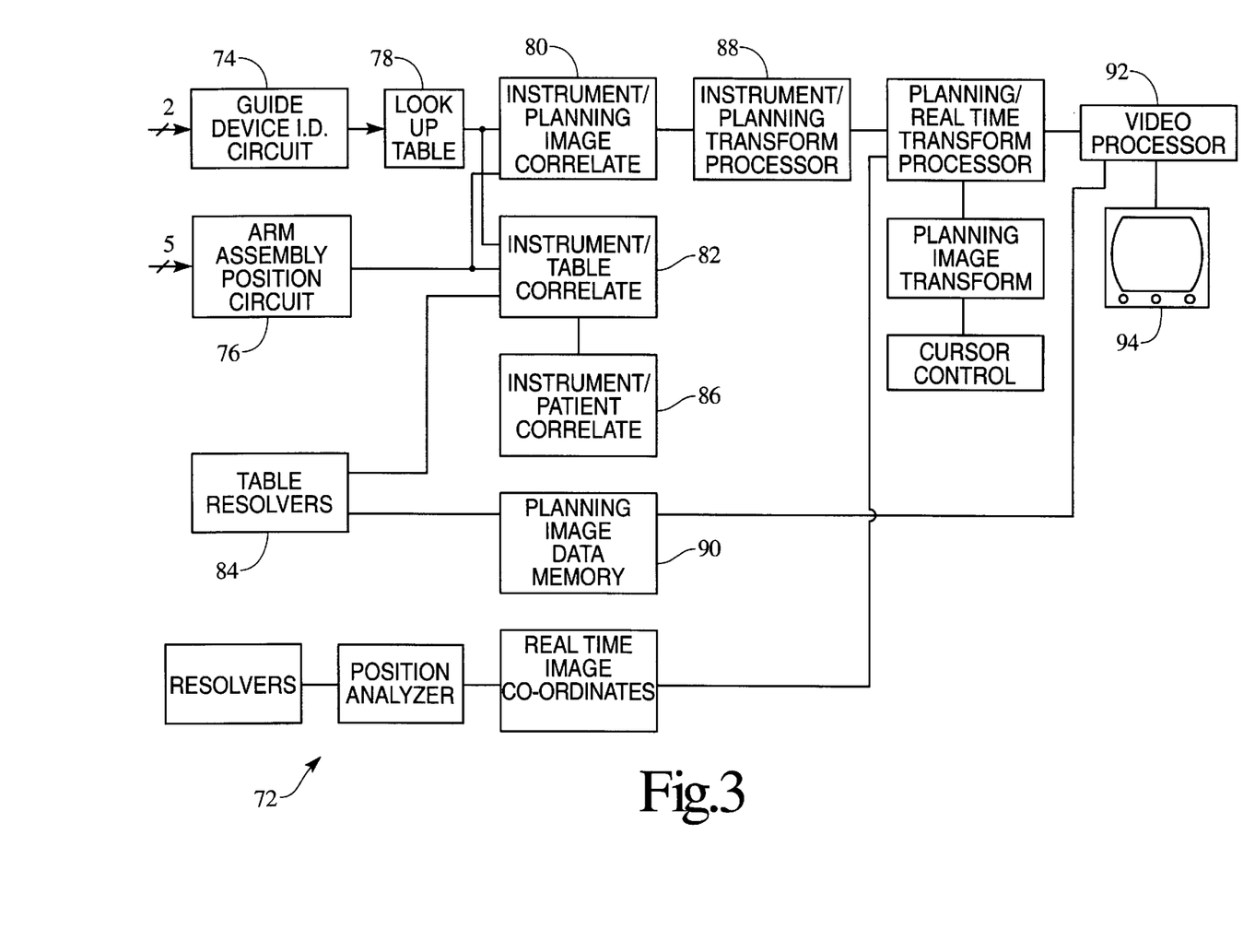
FIG. 3 is a diagrammatic illustration of the planning image processing performed with the apparatus of FIG. 1.

With reference now to FIG. 3, an instrument coordinate circuit 72 determines the position and trajectory of the surgical instrument 36 in instrument space, particularly a coordinate system of the instrument. The instrument coordinate circuit includes a guidance device identification circuit 74 and a mechanical arm assembly position circuit 76. The guidance device identification circuit 74 receives the device identification signal from the one or more guidance devices connected to the mechanical arm and indexes a look up table 78 to retrieve dimensional and functional information. The mechanical arm assembly position circuit 76 is connected with the incremental resolvers on the mechanical arm assembly 30 to receive signals indicative of changes of position and orientation of the mechanical arm in instrument space. An instrument-planning scanner correlating processor 80 determines the correlation or transform between the surgical instrument 36 and the volumetric scanner 18 coordinate systems. The correlation or transform is normally described in terms of a rigid affine transformation from instrument coordinates into scanner coordinates, involving three axis translations and rotations based on a calibration procedure as set forth in our co-pending application filed together with the instant application, entitled "FRAMELESS STEREOTACTIC TOMOGRAPHIC SCANNER FOR IMAGE GUIDED INTERVENTIONAL PROCEDURES", the teachings of which are incorporated herein by reference.

In accordance with the present invention, the surgical planning device and the volumetric scanner are mechanically linked. Therefore, the transform or relationship between the volumetric scanner and the instrument coordinate system needs only to be calibrated once and, thereafter, is predetermined from the mechanical interconnection between the component parts. The touching of calibration markers or the like need only be performed once and subsequently used merely to confirm that the instrument and the CT scanner coordinates have not become misaligned between interventional procedures.

Using analogous mathematics or known mechanical relationships as above, an instrument to patient table correlating processor 82 determines the correlation or transform between the patient table and the surgical instrument. Images of calibration touch points are utilized to derive transforms between patient table space and planning or real time image coordinate systems.

Table resolvers 84 located in the patient table contribute vertical and longitudinal offsets to the correlation between the surgical instrument and the patient table when the table is raised or lowered and when the patient support 12 is moved axially. An instrument to patient correlation processor 86 determines a correlation between the surgical instrument system and a patient coordinate system. This may be done to provide reassurance to an interventionist by placing the surgical instrument on three or more known references points on the patient. Such points might include readily identifiable anatomical structures such as the tip of the nose, distinctive points of bones, fiducial markers that are aligned during the volumetric imaging process, or the like.

In addition to the above, fiducial points on the scanner (e.g., patient support) can be used to verify the accuracy of the point trajectory localizer within the scanner's coordinate system. In the present invention, the patient is movable in conjunction with the patient support (i.e., couch) while maintaining the registration between the localizer, display, and patient volume data set by resolving and reporting the position of the couch to a display sub-system. The resolved movements of the couch are into and out of the gantry (z-axis) and patient support height (y-axis). The patient support position is digitized and fed back to the display system where adjustments are made to maintain the registration.

An instrument to volumetric image coordinate system transform processor 88 receives the correlation or transform from the surgical instrument to planning image processor 80. The instrument to volumetric image processor operates on input position and orientation coordinates in image space to transform them into volumetric image data space and visa versa. Knowing the position of the surgical instrument in volumetric or planning data space enables the instrument position and orientation to be superimposed on the volumetric planning image data.

In accordance with the present invention, during the planning stage of a medical procedure, the patient is positioned in the volumetric planning scanner and a volumetric image is generated. The volumetric image is stored in a volumetric or planning data memory 90. The position of the patient table during the generation of the planning data, particularly as the table moves to generate spiral or slice data, is stored in conjunction with the volumetric planning data such that the data is correlated with the patient table coordinate system. The operator control 24 controls the volume planning image data memory and a video processor 92 such that selected slices, projection images, surface renderings, or other conventional displays of the data are generated for display on a planning image display 94. Preferably, the planning image display includes a pair of transverse axial slices through the patient and a pair of oblique axial and sagittal slices through common points of intersection along a virtual needle line.

During the planning stage before the surgical procedure, the movement of the surgical planning instrument is displayed in the planning image on the interventionist control console 27. The coordinates and trajectory of a virtual surgical needle instrument are conveyed by the instrument to planning image transform processor 88 for conversion into the planning image coordinate system. The location and trajectory of the virtual needle instrument in the planning image coordinate system is communicated to the video processor 92 which superimposes the position and trajectory of the virtual needle on the CT data display. The mechanical arm assembly generates information that is converted to cursor position signals and virtual needle displays which are transformed into the planning image coordinate system and communicated to the video processor 92 to generate a movable cursor point and a virtual needle representation on the planning image display 94. Preferably, multiple cursor positions are displayed at selected points of interest at intersections of concurrently displayed transverse, oblique coronal, and oblique sagittal views on the volumetric image display 94. As the operator moves a manual control virtual needle depth knob 28 through volumetric image data space or as the surgical planning instrument 36 on the mechanical arm assembly 30 is moved over target areas on the patient, or both, the appropriate selective ones of sagittal, coronal, and transverse views on the interventionist control console 27 automatically change correspondingly.

Figure 4:
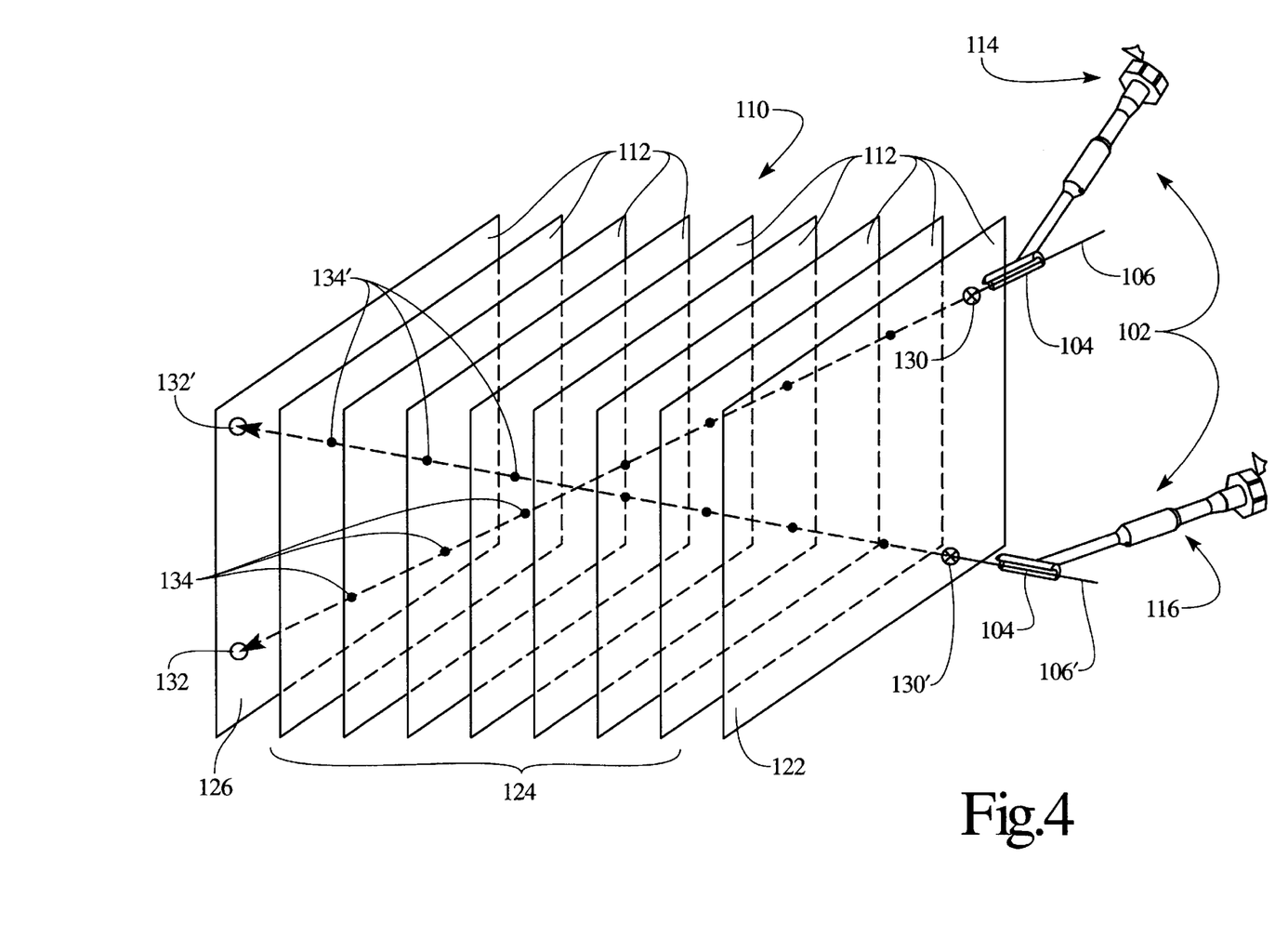
FIG. 4 is a schematic view of an exemplary arrangement of image slice forming a patient image volume data set and illustrating a pair of virtual needle planning paths therethrough.

Turning now to FIG. 4, a representative patient image volume 110 is illustrated schematically as being formed of a plurality of image volume slices 112. As described above, each of the slices 112 are obtained by moving a rotatable X-ray source through a circular path in the imaging apparatus and collecting data from an X-ray translucent material disposed within the bore of the imaging apparatus. Each rotation of the X-ray source generates a single image volume slice 112. Although FIG. 4 illustrates only nine image volume slices to more easily illustrate the present invention, those skilled in the art will recognize that the patient image volume 110 is formed of many more image volume slices 112 such as, for example, eight five (85) slices.

A surgical planning device 102 is shown superimposed upon the patient image volume 110 to help illustrate the virtual needle 120 (FIGS. 5 and 7) formed in accordance with the present invention. In that regard, the surgical planning device 102 includes a "V" groove 104 defining a linear trajectory 106 coaxial with the "V" groove. As shown, the linear trajectory 106 extends through a plurality of image slices including a front image slice 122, a set of intervening image slices 124, and a back image slice 126. Although somewhat artificially, the example shown in FIG. 4 assumes, for purposes of discussion and explanation only, that the intersection of the trajectory and the patient's skin is in the front image slice 122 and the intersection of the trajectory and the target point within the patient is in the back image slice 126. Based on this explanatory hypothetical assumption, the linear trajectory 106 intercepts the front image slice 122 at an entry point 130 and intercepts the back image slice 126 at a target point 132. As shown, the linear trajectory intercepts each of the intervening image slices 124 at a corresponding set of intervening intercept points 134.

As the surgical planning device 102 is moved from the first position 114 to the second position 116, the linear trajectory defined by the "V" groove changes accordingly to a second linear trajectory 106'. With the continued assumption that the intersection of the trajectory and the patient's skin is in the front image slice 122 and the intersection of the trajectory and the target point within the patient is in the back image slice 126, the second linear trajectory 106' defines new entry, target, and intercept points 130', 132', 134' at the front, intervening, and back image slices 122, 124, 126, respectively. In accordance with the present invention, the movement of the surgical planning device 102 adjacent a patient's body on the scanner table is reported to an interventionist on the control and display monitor 27 in the form of multiple cross-sectional views.

Figure 5:
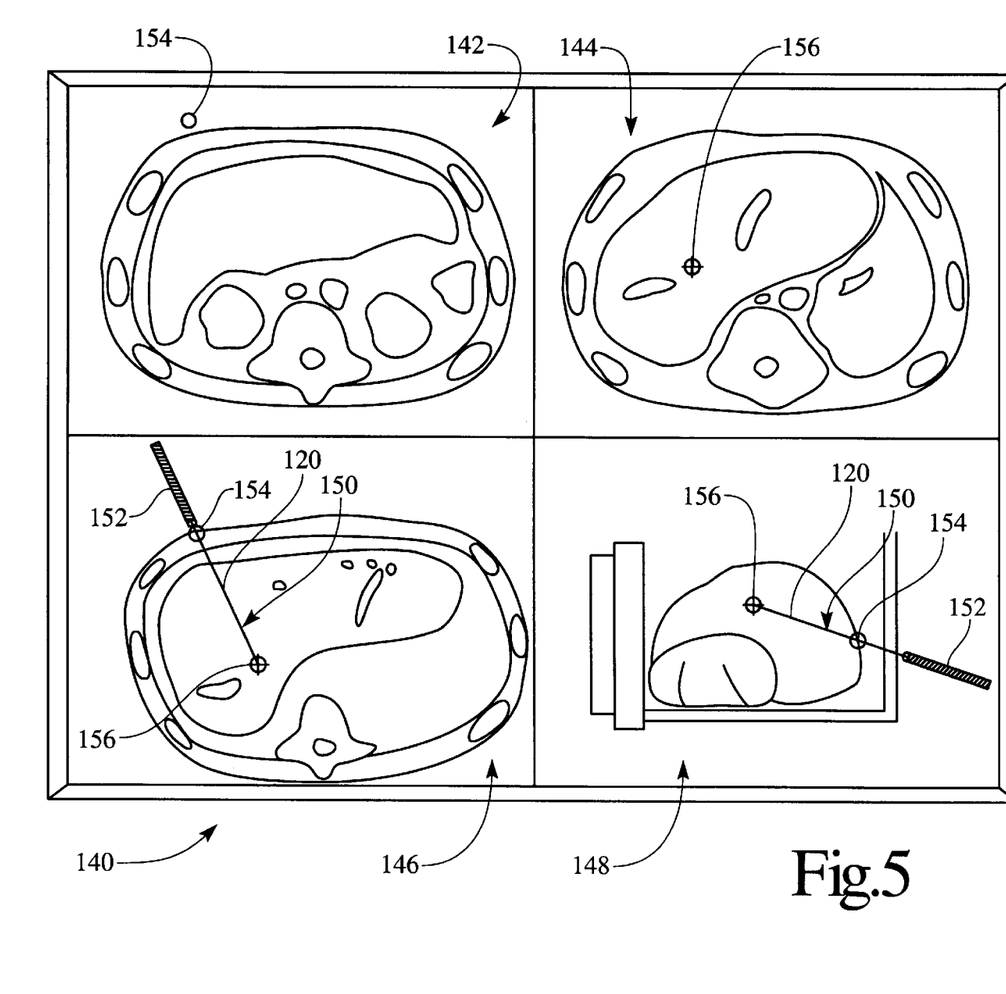
FIG. 5 is an illustration of the preferred set of images of planes extending through the patient image volume data set of FIG. 4.

FIG. 5 illustrates a preferred display 140 in accordance with the present invention. Turning now to that FIGURE, the display 140 is divided into four quadrants or view ports including an upper left transverse axial view port 142, an upper right second transverse axial view port 144, a lower proxy transverse to coronal view port 146, and lastly, a lower proxy sagittal to coronal view port 148. The view ports are selectively displayed. Preferably, the bottom two view ports 146, 148 are multi-planar reformatted (MPR) images that are co-planar with the virtual needle 120 and its path along the linear trajectory 106, 106'. The linear needle 120 is shown in each image 146, 148 as an arrow 150 extending from a thicker line representing a needle guide 152. Since the bottom two view ports holding the multi-planar reformatted images are typically composed of information from multiple image volume slices 112, the virtual needle passes through multiple image volume slices. The upper left transverse axial view port 142 is derived from a one of the image volume slices 112 where the tip of the needle guide is located in space or, at the intersection of the trajectory and the patient's skin. If this position is not in the patient's image volume 110, an out of range message is displayed. In the embodiment illustrated, the upper left transverse axial view port is a representation of the data contained within the front image slice 122. An entry point indicia 154 is positioned on the upper left view port at a point corresponding to the entry point 130 of the virtual needle.

In a similar fashion, the upper right transverse axial view port corresponds to a one of the image volume slices whereat the linear trajectory 106, 106' exits the patient image volume 110. In the exemplary preferred embodiment illustrated, the upper right transverse axial view port 144 is formed from data comprising a first one of the transverse image slices. A target point indicia 156 is located on the upper right transverse view port at a point corresponding to the target intercept point on a second one of the transverse image slices within the patient image volume 110. The target intercept point 132 in the image space is adjustable by an interventionist by operating the manual control knob 28 on the stereotactic arm assembly.

In accordance with the present invention, all four of the view ports are simultaneously updated as the surgical planning device is moved over a patient's body. In that way, an interventionist can appropriately select the best path for inserting a probe or catheter while avoiding bone and damage to soft tissue such as arteries or lungs.

The equations for determining the proximal transverse view displayed on the lower left view port 146 are as follows: a planar MPR section is defined by a point on the plane P, which is the tip of the needle guide, and a normal vector to the plane N.

Let T represent the trajectory of the needle guide. The normal vector Npt (proxy transverse) is determined by:

$$N_{pt} = T \times A_{xy}$$

where $A_{xy}$ is a vector which varies between the X and Y axis. The use of the cross-product of T and Axy insures that N is normal to a plane that intersects T. The vector $A_{xy}$ is a function of T:

$$A_{xy} = -\{T \cdot X_{axis}\}Y_{axis} + (1 - |\{T \cdot X_{axis}\}|)X_{axis}$$

$$= T_x[0, 1, 0] + (1 - |T_{|x}|)[1, 0, 0]$$

$$= [0, T_x, 0] + [1, 0, 0] - [|T_{|x}|, 0, 0]$$

$$= [1 - |T_x|, T_x, 0]$$

Note that this equation yields, case 1, transverse: T=[1,0,0] then $A_{xy}$=[0,1,0] thus $N_{pt}$=[0, 0,−1], case 2, transverse: T=[0,1,0] then $A_{xy}$=[1,0,0] thus $N_{pt}$=[0, 0,−1], case 3, coronal: T=[0,0,1] then $A_{xy}$=[1,0,0] thus $N_{pt}$=[0,1,0], case 4, transverse: T=[1,0,0] then $A_{xy}$=[0,0,1] thus $N_{pt}$=[0, 0,−1].

Cases 1–4 illustrate that the plane stays "proximal transverse" and moves to the coronal orientation as T is moved toward the Z axis. This is achieved without using conditions that check for cross products with zero magnitude (e.g., when T is co-linear with one of the axis). This allows continuous transitions between the planes as the user moves the end-effector along the patient's skin, e.g., from the A-P axis to the lateral axis to the superior-inferior axis, i.e., planar sections do not flip at transitional boundaries between patient axis. It is especially useful to an interventionist to be able to view both the proxy transverse/coronal views in the lower left-hand portion of the screen, together with the proxy saggital/coronal view in the lower right-hand corner of the screen. In accordance with the present invention, the transverse slice at the insertion point of the virtual needle is cross-referenced with the transverse slice of the tip of the virtual needle. The system is therefore better able to provide the interventionist with continuous flowing views of points within the patient's image volume set as the virtual needle is moved relative to the image volume set.

Similarly, for the proxy sagittal $N_{ps}$ sections:

$$N_{ps} = T \times A_{yz}$$

where $A_{yz}$ is a vector which varies between the Z and Y axis. The vector $A_{yz}$ is:

$$\begin{aligned}
A_{yz} &= \{T \cdot Z_{axis}\} Y_{axis} + (1 - |\{T \cdot Z_{axis}\}|) Z_{axis} \\
&= T_z[0, 1, 0] + (1 - |T_z|)[0, 0, 1] \\
&= [0, T_z, 0] + [0, 0, 1] - [0, 0, T_z] \\
&= [0, T_z, 1 - |T_z|]
\end{aligned}$$

Note that in, case 1, coronal: T=[1,0,0] then $A_{yz}$=[0,0,1] thus $N_{ps}$=[0,1,0], case 2, sagittal: T=[0,1,0] then $A_{yz}$=[0,0,1] thus $N_{ps}$=[1,0,0], case 3, sagittal: T=[0,0,1] then $A_{ys}$=[0,1,0] thus $N_{ps}$=[1,0,0].

Figure 6:
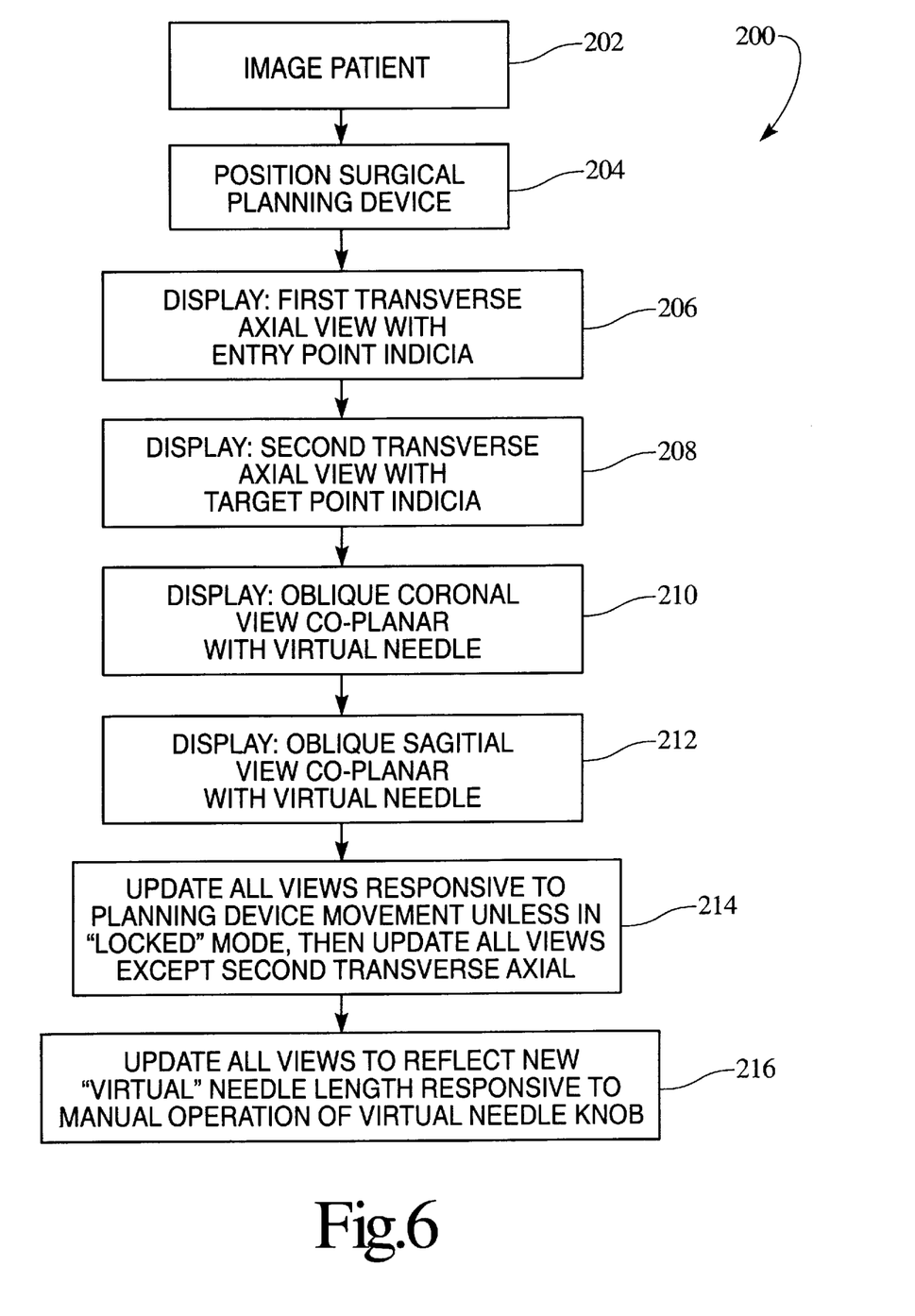
FIG. 6 is a flow chart illustrating the preferred methods of displaying the image shown in FIG. 5; and, FIG. 7 is an illustration of a second preferred set of images of planes extending through the patient image volume data set of FIG. 4 when the present invention is operated in a locked target mode.

Turning now to FIG. 6, a preferred method of planning a minimally invasive surgical procedure 200 in accordance with the present invention will be described. An image volume data set of the patient is obtained at step 202. In accordance with the preferred embodiment of the invention, the imaging device is a CT scanner and the image volume data set is formed of a plurality of two-dimensional image slices of the patient spaced apart along an axial axis substantially aligned with the toe-to-head axis of the patient.

Next, at step 204, a surgical planning device attached to the free end of a stereotactic mechanical arm assembly is positioned adjacent the patient disposed on the imaging device. Preferably, the surgical planning device defines a linear trajectory through a cannula type guide member or, alternatively, an elongated "V" groove defining the trajectory. Since the relationship between the mechanical arm assembly and the imaging device is known by their mechanical interconnection and, further, since the position and orientation of the arm is derived through suitable transfer functions derived using a system calibration performed during installation of the system, the position of the surgical planning device and the orientation of a "virtual needle" is advantageously displayed on a human readable monitor along with the patient image volume data set.

A first transverse axial view of the patient is displayed at step 206 on a first portion of the display monitor. The first transverse axial view provides an insertion point view and is derived from a two-dimensional image slice taken from the plurality of two-dimensional image slices of the patient image volume data set. When a laser planning instrument is used, the point where linear trajectory defined by the surgical planning device intersects the patient's body defines the patient entry point. Alternatively, when a cannula is used, the patient entry point becomes the point where the cannula touches the patient's skin. The patient entry point is illustrated on the first transverse axial view as a small highlighted circle.

Next, at step 208, a second transverse axial view of the patient is displayed on a second portion of the human readable display monitor. The second transverse axial view shows the tip of a virtual needle and corresponds to a second two-dimensional image slice taken from the patient image volume data set where the tip of the linear trajectory defined by the surgical planning device intersects the patient's body at a first target point within the patient. The first target point is highlighted on the display monitor using suitable indicia such as an "X" in either white or other highly visible color.

An oblique axial/coronal view of the virtual needle is displayed at step 210 and, at step 212, an oblique sagittal view of the virtual needle is displayed on the monitor. The oblique axial/coronal view is co-planar with the virtual needle from the patient entry point to the first target point within the patient. Similarly, the oblique coronal/sagittal view is co-planar with the virtual needle from the patient entry point to the first target point within the patient. Each of the oblique axial/coronal and coronal/sagittal views define planes extending through multiple slices of the patient image volume data set.

At step 214, each of the displays on the monitor are updated as the surgical planning device is moved into various positions adjacent the patient's body. Similarly, at step 216, each of the views displayed on the monitor are updated when the virtual needle manual depth control know is adjusted.

Figure 7:
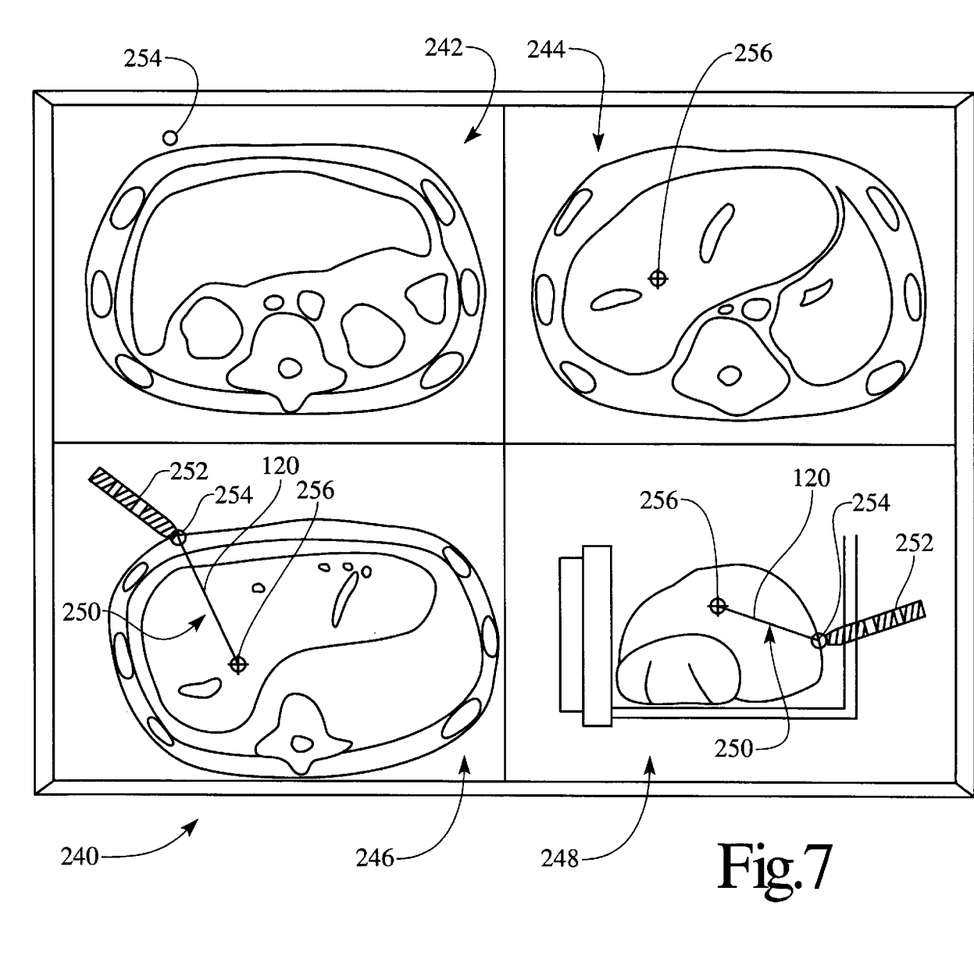

Turning next to FIG. 7, a second mode of the present invention will be illustrated in connection with a "locked target mode" display 240 which is divided into four quadrants or view ports including an upper left transverse axial view port 242, an upper right second transverse axial view port 244, a lower left oblique coronal view port 246, and, lastly, a lower right oblique sagittal view port 248. In the "locked mode," the location of the target point within the patient is selected manually by an interventionist. After selecting the target point within the patient, the stereotactic arm assembly is adjusted to place the surgical planning device at a position and orientation corresponding to a preferred trajectory extending between the fixed target point within the patient and multiple entry points corresponding to multiple positions of the surgical planning device adjacent the patient.

As described above in connection with the first preferred embodiment of the invention, the bottom two view ports 246, 248 are preferably multi-planar reformatted (MPR) images that are co-planar with the virtual needle 120 and its path along a linear trajectory 206. The linear needle 120 is shown in each image 246, 248 as an arrow 250 extending from a thicker line representing a needle guide 252. Since the bottom two view ports holding the multi-planar reformatted images are typically composed of information from multiple image slices 112, the virtual needle passes through multiple image volume slices. The upper left transverse axial view port 242 is derived from a one of the plurality of image volume slices 112 where the linear trajectory intercepts the patient's skin. An entry point indicia 254 is positioned on the upper left view port at a point corresponding to the entry point 130 of the virtual needle 120.

In a similar fashion, the upper right transverse axial view port corresponds to an image volume slice whereat the linear trajectory intercepts the target point within the patient. In the "locked mode" embodiment illustrated, the upper right transverse axial view port 244 remains fixed in display content to reflect that the target point remains fixed in the patient image volume data set as the surgical planning device is manipulated into various orientations and positions. In that regard, a target point indicia 256 is located on the upper right transverse view port at a point corresponding to the target intercept point selected by the interventionist within the patient image volume data set. The target intercept point is adjustable by an interventionist by operating the manual depth control knob on the stereotactic arm assembly while the apparatus is in the "locked" mode.

In accordance with the second preferred embodiment of the present invention, all of the view ports are simultaneously updated, except for the upper right transverse axial view which illustrates the fixed target point. Preferably, in the "locked mode," the tip of the virtual needle is anchored to a target point selected by an operator. Accordingly, virtual needle trajectories are defined as insertion-point-to-target trajectories by moving the actual and virtual insertion points along the patient's skin or each new insertion point defines a virtual needle trajectory defined as a line between the insertion point and the target point or the tip of the virtual needle. However, this trajectory is not necessarily coincident with the trajectory of the surgical planning device. Therefore, according to the second preferred embodiment of the invention, the virtual needle guide 252 is illustrated as a dashed line when the trajectory of the planning device is not coaxial with the trajectory of the virtual needle extending between the patient entry point and the target point within the patient selected by the interventionist.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. A method of planning a minimally invasive surgical procedure for introducing an object along a trajectory from a patient entry point to a target point within the patient, the method comprising the steps of:

using an imaging device, scanning the patient to generate an image volume data set of an area of the patient, the image volume data set being formed of a plurality of two-dimensional image slices of the patient spaced apart along an axial axis substantially aligned with the toe-to-head axis of the patient;

using a stereotactic mechanical arm assembly mounted on one end in a fixed relationship to the imaging device and having a surgical planning device defining a linear trajectory on the other end of the arm, positioning the surgical planning device in a first position adjacent the patient on the imaging device;

displaying a first transverse axial view of the patient on a first portion of a display device, the first transverse axial view of the patient being a display of a first two-dimensional image slice from said plurality of two-dimensional image slices of the patient where the linear trajectory intersects the patient's body defining a first patient entry point;

displaying a second transverse axial view of the patient on a second portion of the display device, the second transverse axial view of the patient being a display of a second two-dimensional image slice from said plurality of two-dimensional image slices of the patient where the linear trajectory intersects the patient's body at a first target point within the patient; and, displaying a first oblique view of the patient on the display device, the first oblique view of the patient being a display of a first plane within said image volume data set co-planar with a line defined by said trajectory.

2. The method of planning a minimally invasive surgical procedure according to claim 1, further comprising the step of:

while moving said surgical planning device from said first position adjacent the patient to a second position adjacent the patient, simultaneously updating at least a one of said first and second transverse axial views so that i) the first transverse axial view corresponds to a first two-dimensional image slice from said plurality of two-dimensional image slices of the patient where the linear trajectory with the surgical planning device at said second position intersects the patient's body defining a second patient entry point, and ii) the second transverse axial view corresponds to a second two-dimensional image slice from said plurality of two-dimensional image slices of the patient where the linear trajectory with the surgical planning device at said second position intersects the patient's body at a second target point within the patient.

3. The method of planning a minimally invasive surgical procedure according to claim 2 wherein the step of simultaneously updating at least a one of said first and second transverse axial views includes simultaneously updating both of said first and second transverse axial views.

4. The method of planning a minimally invasive surgical procedure according to claim 1 further comprising the step of:

without moving said surgical planning device, manually operating a virtual needle depth control member to change said second transverse axial view of the patient on said second portion of the display device to correspond to a third two-dimensional image slice from said plurality of two-dimensional image slices of the patient where the linear trajectory intersects the patient's body at a second target point within the patient.

5. The method of planning a minimally invasive surgical procedure according to claim 4 wherein the step of manually operating said virtual needle depth control member includes:

manually operating the virtual needle depth control member in a first direction to reduce a distance between the patient entry point and the target point within the patient; and, manually operating the virtual needle depth control member in a second direction to increase a distance between the patient entry point and the target point within the patient.

6. The method of planning a minimally invasive surgical procedure according to claim 1 further comprising the step of:

while moving said surgical planning device from a first position adjacent the patient to a second position adjacent the patient, updating only said first transverse axial view of the patient on said first portion of the display device so that i) the first transverse axial view corresponds to a first two-dimensional image slice from said plurality of two-dimensional image slices of the patient where the linear trajectory intersects the patient's body with the surgical planning device at said second position, defining a second patient entry point, and ii) the second transverse axial view remains fixed corresponding to said first two-dimensional image slice from said plurality of said two-dimensional image slices of the patient.

7. The method of planning a minimally invasive surgical procedure according to claim 1 wherein the step of scanning the patient includes scanning the patient at a first position on the imaging machine.

8. The method of planning a minimally invasive surgical procedure according to claim 1 further comprising the steps of:

using said stereotactic mechanical arm assembly, positioning the surgical planning device in a second position adjacent the patient on the imaging device;

displaying a third transverse axial view of the patient on said first portion of a display device, the third transverse axial view of the patient being a display of a third two-dimensional image slice from said plurality of two-dimensional image slices of the patient where the linear trajectory defined by the planning device in said second position intersects the patient at a second patient entry point; and, displaying a fourth transverse axial view of the patient on said second portion of the display device, the fourth transverse axial view of the patient being a display of a fourth two-dimensional image slice from said plurality of two-dimensional image slices of the patient where the linear trajectory defined by the planning device in said second position intersects the patient at a second target point within the patient.

9. The method of planning a minimally invasive surgical procedure according to claim 1, further comprising the step of:

displaying a second oblique view of the patient on the display device, the second oblique view of the patient being a display of a second plane through said image volume data set that is co-planar with said line defined by the trajectory.

10. The method of planning a minimally invasive surgical procedure according to claim 9 wherein:

the step of displaying said first oblique view of the patient includes displaying a oblique axial/coronal view of the patient on a third portion of the display device; and, the step of displaying said second oblique view of the patient includes displaying a oblique coronal/sagittal view of the patient on a fourth portion of the display device.

11. A method of planning a minimally invasive surgical procedure for introducing an object along a trajectory from a patient entry point to a target point within the patient, the method comprising the steps of:

using an imaging device, scanning the patient to generate an image volume data set of an area of the patient;

using a stereotactic assembly mounted on one end in a fixed relationship to the imaging device and having a surgical planning device defining a linear trajectory on the other end of the assembly, positioning the surgical planning device adjacent the patient;

displaying a first transverse axial view of the patient on a first portion of a display device, the first transverse axial view of the patient being a display of a first two-dimensional image slice from said image volume data set taken where the linear trajectory intersects the patient defining a patient entry point;

displaying a second transverse axial view of the patient on a second portion of the display device the second transverse axial view of the patient being a display of a second two-dimensional image slice from said image volume data set taken where the linear trajectory intersects the patient at a first target point within the patient;

displaying a first oblique axial/coronal view of the patient on a third portion of the display device, the first oblique axial/coronal view of the patient being a display of a first plane within said image volume data set co-planar with said trajectory from said patient entry point to said target point within the patient; and, displaying a first oblique coronal/sagittal view of the patient on a fourth portion of the display device, the first oblique coronal/sagittal view of the patient being a display of a second plane through said image volume data set that is co-planar with the trajectory between said patient entry point and the first target point within the patient and is substantially sagittal in orientation.

12. The method of planning a minimally invasive surgical procedure according to claim 11 further comprising the step of:

while moving said surgical planning device from a first position adjacent the patient to a second position adjacent the patient, simultaneously updating each of said first and second transverse axial views of the patient, said first oblique axial/coronal view of the patient, and said first oblique coronal/sagittal view of the patient.

13. The method of planning a minimally invasive surgical procedure according to claim 11, further comprising the step of:

while moving said surgical planning device from a first position adjacent the patient to a second position adjacent the patient, simultaneously updating at least a one of said first and second transverse axial views so that i) the first transverse axial view corresponds to a first two-dimensional image from said image volume data set of the patient where the linear trajectory, with the surgical planning device at said second position, intersects the patient defining a second patient entry point, and ii) the second transverse axial view corresponds to a second two-dimensional image from said image volume data set of the patient where the linear trajectory, with the surgical planning device at said second position, intersects the patient at a second target point within the patient.

14. The method of planning a minimally invasive surgical procedure according to claim 13 wherein the step of simultaneously updating at least a one of said first and second transverse axial views includes simultaneously updating both of said first and second transverse axial views.

15. The method of planning a minimally invasive surgical procedure according to claim 11 further comprising the step of:

without moving said surgical planning device, manually operating a virtual needle depth control member to change said second transverse axial view of the patient on said second portion of the display device to correspond to a third two-dimensional image from said image volume data set of the patient where the linear trajectory intersects the patient at a second target point within the patient.

16. The method of planning a minimally invasive surgical procedure according to claim 15 wherein the step of manually operating said virtual needle depth control member includes:
   manually operating the virtual needle depth control member in a first direction to reduce a distance between the patient entry point and the target point within the patient; and,
   manually operating the virtual needle depth control member in a second direction to increase a distance between the patient entry point and the target point within the patient.

17. The method of planning a minimally invasive surgical procedure according to claim 11 further comprising the step of:
   while moving said surgical planning device from a first position adjacent the patient to a second position adjacent the patient, updating only said first transverse axial view of the patient on said first portion of the display device so that i) the first transverse axial view corresponds to a first two-dimensional image from said image volume data set of the patient where the linear trajectory intersects the patient's body with the surgical planning device at said second position, defining a second patient entry point, and ii) the second transverse axial view remains fixed corresponding to said first two-dimensional image from said image volume data set of the patient.

18. The method of planning a minimally invasive surgical procedure according to claim 11, further comprising the step of:
   while moving said surgical planning device from a first position adjacent the patient to a second position adjacent the patient, simultaneously updating at least a one of said first oblique axial/coronal view and said first oblique coronal/sagittal view so that the at least one updated view remains co-planar with said line defined by the trajectory.

19. A method of planning a surgical procedure for inserting an object into a patient along a surgical planning trajectory from an entry point on the patient to a target point within the patient, the method comprising the steps of:
   using an imaging device, scanning the patient to generate an image volume data set of an area of the patient;
   using an associated surgical planning device disposed in a first position relative to the patient, defining a linear planning trajectory extending from the planning device and through the patient;
   displaying a first oblique sectional image of the patient co-planar with the linear planning trajectory, the first sectional image being derived from said image volume data set based on said first position of the surgical planning device relative to the patient; and,
   displaying a second oblique sectional image of the patient co-planar with the linear planning trajectory, the second sectional image being derived from said image volume data set based on said first position of the surgical planning device relative to the patient.

20. The method of planning a surgical procedure according to claim 19 wherein:
   the step of displaying said first oblique sectional image of the patient includes displaying a first oblique axial/coronal view of the patient co-planar with the linear planning trajectory; and,
   the step of displaying said second oblique sectional image of the patient includes displaying a first oblique coronal/sagittal view of the patient co-planar with the linear planning trajectory.

21. The method of planning a surgical procedure according to claim 20 further including the step of:
   while moving the associated surgical planning device from said first position relative to the patient towards a second position relative to the patient, simultaneously updating at least a one of said first and second sectional images of the patient so that the first and second sectional images of the patient remain co-planar with the linear planning trajectory defined by the associated surgical planning device.

22. The method of planning a surgical procedure according to claim 20 further including the steps of:
   displaying a first transverse axial view of the patient, the first transverse axial view being a display of a two-dimensional image of the patient where said planning trajectory intersects the patient at said entry point; and,
   displaying a second transverse axial view of the patient, the second transverse axial view being a two-dimensional image of the patient where said planning trajectory intersects the patient at said target point.

23. A method of planning an interventional procedure for inserting a surgical tool into a patient along an interventional planning trajectory from a patient entry point towards a target point within the patient, the method comprising the steps of:
   providing an image volume data set representative of a multi-dimensional view of the patient;
   defining a linear interventional planning trajectory extending from a first patient entry point to a first target point;
   deriving first and second sectional images of the patient from said image volume data set, the first and second sectional images intersecting at a line defined by said linear interventional planning trajectory; and,
   displaying at least one of the first and second sectional images.

24. The method of planning an interventional procedure according to claim 23 wherein:
   the step of deriving said first and second sectional images of the patient include deriving a first oblique axial/coronal view of the patient as said first sectional image and deriving a first oblique coronal/sagittal view of the patient as said second sectional image; and,
   the step of displaying at least one of said the first and second sectional images includes displaying at least one of said first oblique axial/coronal view and said first oblique coronal/sagittal view.

25. A surgical procedure planning apparatus for use in inserting an object into a patient along a surgical planning trajectory from an entry point on the patient to a target point within the patient, the planning apparatus comprising:
   an imaging device for scanning the patient to generate an image volume data set of an area of the patient;
   a surgical planning device, disposed in a first position relative to the patient, for defining a linear planning trajectory extending from the planning device and through the patient;
   means for displaying a first oblique sectional image of the patient co-planar with the linear planning trajectory, the first sectional image being derived from said image volume data set based on said first position of the surgical planning device relative to the patient; and, means for displaying a second oblique sectional image of the patient co-planar with the linear planning trajectory, the second sectional image being derived from said image volume data set based on said first position of the surgical planning device relative to the patient.

26. The surgical procedure planning apparatus according to claim 25 further comprising:

means for displaying said first oblique sectional image of the patient as a first oblique axial/coronal view of the patient co-planar with the linear planning trajectory; and, means for displaying said second oblique sectional image of the patient as a first oblique coronal/sagittal view of the patient co-planar with the linear planning trajectory.

27. The surgical procedure planning apparatus according to claim 26 further comprising:

means for simultaneously updating at least a one of said first and second sectional images of the patient so that the first and second sectional images of the patient remain co-planar with the linear planning trajectory defined by the associated surgical planning device while moving the associated surgical planning device from said first position relative to the patient towards a second position relative to the patient.

28. The surgical procedure planning apparatus according to claim 26 further comprising:

means for displaying a first transverse axial view of the patient, the first transverse axial view being a display of a two-dimensional image of the patient where said planning trajectory intersects the patient at said entry point; and, means for displaying a second transverse axial view of the patient, the second transverse axial view being a two-dimensional image of the patient where said planning trajectory intersects the patient at said target point.

29. A method of surgical procedure planning for planning insertion of an object into a patient along a surgical planning trajectory from an entry point on the patient to a target point within the patient, the method comprising the steps of:

scanning the patient to generate an image volume data set of an area of the patient;

defining a linear planning trajectory extending in a first position through said image volume data set of the area of the patient;

displaying a first oblique sectional image of the patient co-planar with the linear planning trajectory, the first sectional image being derived from said image volume data set based on said first position of the linear planning trajectory relative to said area of the patient; and, displaying a second oblique sectional image of the patient co-planar with the linear planning trajectory, the second sectional image being derived from said image volume data set based on said first position of the linear planning trajectory relative to said area of the patient.

30. The method according to claim 29 wherein:

the step of displaying said first oblique sectional image of the patient includes the step of displaying a first oblique axial/coronal view of the patient co-planar with the linear planning trajectory in said first position; and, the step of displaying said second oblique sectional image of the patient includes displaying a coronal/sagittal view of the patient co-planar with the linear planning trajectory in said first position.

31. The method according to claim 29 further including the step of, while moving the linear planning trajectory from said first position towards a second position relative to the area of the patient in said image volume data set, simultaneously updating at least a one of said first and second sectional images of the patient so that the first and second sectional images of the patient remain co-planar with the linear planning trajectory.

32. The method according to claim 29 further including the steps of:

displaying a first transverse axial view of the patient, the first transverse axial view being a display of a two-dimensional image of the patient where said planning trajectory in said first position intersects the patient at said entry point; and, displaying a second transverse axial view of the patient, the second transverse axial view being a two-dimensional image of the patient where the planning trajectory in said first position intersects the patient at said target point.

33. The method according to claim 32 further including the steps of:

selecting on a display screen, a second target point within said patient; and, displaying a third transverse axial view of the patient, the third transverse axial view being a two-dimensional image of the patient where said planning trajectory intersects the patient at said second target point.

34. The method according to claim 29 further including the steps of:

selecting on a display screen, a second target point within said patient;

updating said first oblique sectional image of the patient based on said, linear planning trajectory extending from said entry point on the patient to said second target point within said patient; and, updating said second oblique sectional image of the patient based on said linear planning trajectory extending from said entry point on the patient to said second target point within said patient.

35. The method according to claim 34 further including the step of, while moving said second target point on said display screen, simultaneously updating at least one of said first oblique sectional image of the patient and said second oblique sectional image of the patient to show said second target point moved on said display screen.

36. The method according to claim 35 wherein the step of scanning the patient includes the step of magnetic resonance image scanning the patient to generate said image volume data set of said area of the patient.

* * * * *